United States Patent [19]

Quarles

[11] Patent Number: 4,927,811

[45] Date of Patent: May 22, 1990

[54] METHOD AND COMPOSITION FOR IMPROVED ANIMAL HUSBANDRY

[75] Inventor: Carey L. Quarles, Fort Collins, Colo.

[73] Assignee: Coors Biotech, Inc., Westminster, Colo.

[21] Appl. No.: 271,931

[22] Filed: Nov. 15, 1988

[51] Int. Cl.$^5$ .................... A61K 33/00; A61K 31/70
[52] U.S. Cl. .......................................... 514/23; 424/92; 424/442; 426/2; 426/658; 514/54; 514/867
[58] Field of Search ............... 514/23, 54, 867; 426/2, 426/658; 424/92, 442

[56] References Cited

U.S. PATENT DOCUMENTS

| | | | |
|---|---|---|---|
| 3,728,132 | 4/1973 | Tsuyama et al. | 426/658 |
| 4,613,377 | 9/1988 | Yamazaki et al. | 127/39 |
| 4,681,771 | 7/1987 | Adachi et al. | 426/658 |
| 4,693,898 | 9/1987 | Nakatomi et al. | 426/19 |
| 4,696,916 | 9/1987 | Yabushita et al. | 514/23 |
| 4,788,065 | 11/1988 | Nakamura et al. | 426/2 |

FOREIGN PATENT DOCUMENTS

| | | |
|---|---|---|
| 2105338 | 3/1983 | United Kingdom . |
| 2072679 | 11/1983 | United Kingdom . |
| 2179946 | 3/1987 | United Kingdom . |

OTHER PUBLICATIONS

Oku et al., "Nondigestibility of a New Sweetener, 'Neosugar', in the Rat", Journal of Nutrition, vol. 114, No. 9, pp. 1574-1581 (1984).

*Primary Examiner*—Ronald W. Griffin
*Attorney, Agent, or Firm*—Sheridan, Ross & McIntosh

[57] ABSTRACT

The present invention relates to a method and composition for increasing the breast weight to body weight ratio in poultry. The present invention also relates to methods and compositions for reducing mortality and reducing the occurrence of air sac lesions in poultry and livestock. The compositions of the present invention include fructooligosaccharides, and in particular, fructooligosaccharides produced by the action of a fructosyl transferase enzyme on a sucrose substrate. The methods of the present invention involve the administration of compositions including fructooligosaccharides to poultry and livestock. The fructooligosaccharides are preferably administered by incorporation into the poultry or livestock's food supply.

18 Claims, No Drawings

METHOD AND COMPOSITION FOR IMPROVED ANIMAL HUSBANDRY

FIELD OF THE INVENTION

The present invention relates generally to improved methods and compositions of animal husbandry to produce healthier and more economical poultry and livestock.

BACKGROUND OF THE INVENTION

Consumers of poultry meat primarily prefer the breast meat portion of poultry. Because of this preference, strains of poultry have been bred to produce high proportions of breast meat as a percentage of total body weight. In contrast to such methods of genetic control of poultry body structure, however, no methods of environmental control of breast weight to body weight ratio are known to be effective. Development of methods of environmental control of poultry breast weight to body weight ratio, therefore, are desirable.

In addition to concerns about poultry breast weight to body weight ratio, modern animal husbandry practices, in an effort to maximize production, tend to crowd large numbers of poultry or livestock into relatively small breeding areas. Such crowding produces stress for the animals which creates undesirable effects on the animals. For instance, high levels of stress can cause increased mortality and increased occurrence of air sac lesions. The efficiency of breeding operations is negatively affected by such problems and results in the loss of substantial amounts of money throughout the industry. Accordingly, a need exists for methods of animal husbandry to reduce mortality and occurrence of air sac lesions in poultry and livestock.

The present invention relates to a method and composition for increasing the breast weight to body weight ratio of poultry which involves the use of an effective compound. This effective compound is also useful for reducing mortality and occurrence of air sac lesions in poultry and livestock.

Specific embodiments of the effective compound of the present invention are produced by Meiji Seika Kaisha, Ltd. of Japan, under the trade name "Neosugar". For example, in Oku, et al., Non-digestibility of a New Sweetener, "Neosugar," in the Rat, J. of Nutrition, v. 114, No. 9, pp. 1575–81 (1984), Neosugar is described as a mixture of 1-kestose, nystose, and 1-fructofuranosyl nystose which was studied for digestibility in rats. See also, U.S. Pat. No. 4,681,771 to Adachi, et al. (July 21, 1987), U.K. Pat. No. GB 2,072,679 and U.K. Pat. No. GB 2,150,338, owned by Meiji Seika, which discuss the use of Neosugar compositions as low-cariogenic and low-calorie sweeteners.

Neosugar has also been identified by Meiji Seika as a useful composition for remedying scours in young domestic animals to increase their weight in their growing period in U.S. Pat. No. 4,734,402 (Mar. 29, 1988). This patent also discloses that the use of fructooligosaccharides with poultry improves body weight gain and feed conversion. European Patent Application No. 85109590.1 identifies similar effects of "inulooligosaccharides" on animals.

U.S. patent application Ser. No. 107,115 (filed on Oct. 13, 1987), which is commonly owned with the present invention, discloses the use of Neosugar for inhibiting the growth of Salmonella and, in particular, for preventing or controlling the intestinal colonization of food animals by Salmonella.

Neosugar is produced by the enzymatic reaction of a fructosyl transferase enzyme acting on a sucrose substrate For example, see U.S. Pat. No. 4,681,771. Other uses and methods for producing similar fructo-oligosaccharide-containing compositions are known. See U.S. Pat. Nos. 4,317,880, 4,335,207, and 4,356,262 which are owned by CPC International, Inc. These references describe the production of a mixture of fructooligosaccharides for use as an intermediate substrate for the subsequent production of high fructose-containing syrups.

No known references disclose the use of Neosugar for increasing the breast weight to body weight ratio in poultry or for decreasing mortality and occurrence of air sac lesions in poultry and livestock.

SUMMARY OF THE INVENTION

The present invention includes methods for improved animal husbandry to produce healthier and more economical poultry and livestock. In particular, the present invention relates to a method for raising poultry having a high breast weight to body weight ratio. Additionally, the present invention relates to methods for raising poultry and livestock having decreased mortality and decreased occurrence of air sac lesions. The methods of the present invention generally involve feeding to animals a composition including fructooligosaccharides.

The fructooligosaccharides are more specifically characterized as sucrose molecules having from 1 to 8 fructose residues. This class of compounds is exemplified by a product, Neosugar, which includes as components 1-kestose, nystose, and 1-fructofuranosylnystose.

Other aspects of the present invention include feed compositions for increasing the breast weight to body weight ratio of poultry and for decreasing mortality and decreasing occurrence of air sac lesions in poultry and livestock. The compositions have a nutritive component and a component which includes fructooligosaccharides in amounts effective to promote the desired effects.

DETAILED DESCRIPTION

One aspect of the present invention involves a method for increasing the breast weight as a percentage of body weight of poultry to produce poultry having the desirable characteristic of a high breast weight to body weight ratio. Another aspect of the invention is a method for decreasing the mortality of poultry and livestock for the more efficient practice of animal husbandry. A further aspect of the invention is a method for decreasing the occurrence of air sac lesions for the production of healthier poultry and livestock. The methods of the present invention and feed compositions of the present invention involve the use of an effective composition which includes fructooligosaccharides. The effective composition and specific embodiments of the effective composition will be discussed in more detail below. However, for the present, all embodiments will be generally referred to as the "effective composition."

It has been found that by incorporating the effective composition into the diets of chickens, the breast weight to body weight ratio of chickens is improved over controls and over chickens that have received only antibiotics. This method of promoting the increase of the breast weight to body weight ratio is effective for all types of poultry.

This method can be practiced by feeding to poultry the effective composition mixed with food rations. Alternatively, the effective composition can be fed alone, without mixing it into food rations, or introduced by mixing it in poultry drinking water sources. In these latter two embodiments, the effective composition should be used in amounts comparable to those when it is mixed with food rations, as described below.

The present method of increasing the poultry breast weight to body weight ratio can be conducted by administering the effective composition throughout the entire lifetime of the poultry or during any portion or intermittent portions thereof. The present method is most effective when conducted during the poultry's entire lifetime. When conducted for less than the entire lifetime the method is preferably conducted for long portions of the poultry's lifespan.

While the present method of increasing poultry breast weight to body weight ratios is effective, no mechanism or explanation for this effect is known or hypothesized. However, this method is not intended to be limited or circumscribed by the lack of a known mechanism or by any particular hypothesized mechanism which may hereafter be developed.

The present method of increasing poultry breast weight to body weight ratios can also be conducted in conjunction with other known methods of animal husbandry. For example, the incorporation of antibiotics or other chemical agents, such as coccidiostat, are useful for maintaining healthy, uninfected poultry. Additionally, the use of vitamins or other feed supplements are useful for growing healthier poultry.

As stated above, the present invention also includes a method for decreasing the mortality of poultry and livestock and a method for decreasing the occurrence of air sac lesions in poultry and livestock. By incorporating the effective composition in the diets of poultry and livestock, the effects described above are observed. These methods are effective for all types of poultry and livestock.

The methods for decreasing the mortality and occurrence of air sac lesions in poultry and livestock can be practiced by feeding to poultry and livestock the effective composition mixed with food rations. Alternatively, the effective composition can be fed alone, without mixing it into food rations, or introduced by mixing it in drinking water sources. In these latter two embodiments, the effective composition should be used in amounts comparable to those when it is mixed with food rations, as described below. The present methods of decreasing the mortality and occurrence of air sac lesions in poultry and livestock can be conducted by administering the effective composition throughout the entire lifetime of the poultry and livestock or during any portion or intermittent portions thereof. These methods are most effective when conducted during the poultry or livestock's entire lifetime. When conducted for less than the entire lifetime, these methods are preferably conducted for long portions of the poultry or livestock's lifetime.

While the present methods of decreasing the mortality and occurrence of air sac lesions in poultry and livestock are effective, no mechanism or explanation for these effects is known or hypothesized. However, these methods are not intended to be limited or circumscribed by the lack of a known mechanism or by any particular hypothesized mechanism which may hereafter be developed. The present methods of decreasing mortality and the occurrence of air sac lesions in poultry and livestock can also be conducted in conjunction with other known methods of animal husbandry. For example, the incorporation of antibiotics or other chemical agents, such as coccidiostat, are useful for maintaining healthy, uninfected poultry and livestock. Additionally, the use of vitamins or other feed supplements are useful for growing healthier poultry and livestock.

The effective composition of the present invention includes fructooligosaccharides. The term "fructooligosaccharide", as used herein, refers to a trisaccharide having one or more fructose residues. This class includes mixtures of oligosaccharide molecules comprised of sucrose having from 1 to 8 fructose residues. The fructose residues are preferably attached by a beta 2-1 bond. The class is exemplified by the fructooligosaccharides in the Neosugar produced by Meiji Seika and as described in U.S. Pat. No. 4,681,771, which is incorporated herein by reference herein.

Neosugar is a mixture including 1-kestose, nystose, and 1-fructofuranosyl-nystose. Neosugar, as used herein, is more particularly defined as having between about 20% by weight and about 40% by weight 1-kestose, between about 20% by weight and about 55% by weight nystose, and between about 5% by weight and about 15% by weight 1-fructofuranosyl-nystose. The remaining portion of a Neosugar mixture can include between about 4% by weight and about 45% by weight of a mixture of glucose and sucrose. In one form, Neosugar G, the composition is a 75% syrup having between about 40% by weight and about 50% by weight of a mixture of glucose and sucrose, between about 20% by weight and about 30% by weight 1-kestose, between about 20% by weight and about 30% by weight nystose, and between about 2% by weight and about 8% by weight 1-fructofuranosyl-nystose. In another form, Neosugar P, the composition is either a 75% syrup or a powder having between about 2% by weight and about 6% by weight of a mixture of glucose and sucrose, between about 30% by weight and about 40% by weight 1-kestose, between about 45% by weight and about 55% by weight nystose, and between about 5% by weight and about 15% by weight 1-fructofuranosyl-nystose. The structures of 1-kestose, nystose, and 1-fructofuranosyl-nystose are provided below.

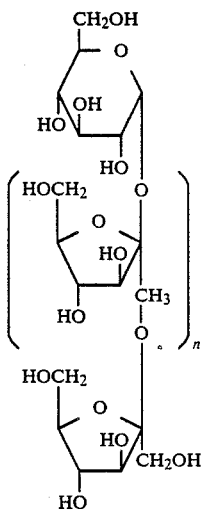

where:
n=1 for 1-kestose
n=2 for nystose
n=3 for 1-fructofuranosyl nystose

Neosugar can be produced by the action of fructosyl transferase on sucrose to produce a mixture of 1-kestose, nystose, and 1-fructofuranosyl nystose. Neosugar G, for example, can be produced by subjecting the product of fructosyl transferase activity to decoloration, filtration, desalting, and concentration. Neosugar G can be further purified with an ion exchange resin to produce Neosugar P. Other methods for further purifying Neosugar are known. For example, in GB No. 2,179,946A, which is incorporated herein by reference, discloses a process for producing a composition having up to about 97% fructooligosaccharides. The process in GB No. 2,179,946A involves a fructosyl transferase reaction and either a subsequent fermentation step to assimilate residual glucose or a subsequent enzymatic reaction to convert residual glucose. It is also contemplated that the use of purified individual fructooligosaccharides or mixtures thereof are within the scope of the present invention.

Certain fungi, such as, Aspergillus and Aureobasidium, as well as other microorganisms are known to produce the enzyme fructosyl transferase. Fructosyl transferases which produce oligosaccharides are also known to be produced by chicory plant and by onion plant. See Singh et al., *Substrate Specificity of Fructosyl Transferase From Chicory Roots*, Phytochemistry vol. 10, pp. 2037–39 (1971) and Henry et al., *Sucrose: Sucrose Fructosyltransferase and Fructan:Fructan Fructosyltransferase From Allium Cepa*, Phytochemistry vol. 19, pp. 1017–20 (1980). The present invention, however, is not intended to be limited to the production of fructooligosaccharides by a fructosyl transferase from any particular source of microorganism or plant. In addition, fructooligosaccharides for use in the present invention can be produced by chemical methods. For example, U.S. Pat. No. 4,613,377 to Yamazaki, et al. describes a process for producing fructooligosaccharides by the hydrolysis of inulin by heating an aqueous solution containing inulin at a temperature of about 70° C. to about 100° C. U.S. Pat. No. 4,613,377 is incorporated herein by reference.

In preferred embodiments of the present methods, the effective composition is fed to poultry or livestock to obtain the desired beneficial result of the methods of the present invention. The preferred method of introduction is to mix the effective composition with nutritive feed material for the animal. It is contemplated, however, that the effective composition can either be mixed with the nutritive feed material or fed to the animal separately. In either embodiment, the effective composition must be provided in an amount effective to obtain the desired result. The amount will vary depending upon the size of the food animal. Poultry will require smaller quantities of the effective composition than, for example, beef to attain the same effect. Effective amounts can readily be determined by experimentation.

The feed compositions of the present invention include, as one component, the effective composition. The feed compositions also include some material which is nutritive for the animal to which the feed composition is fed. Typically, for most poultry and livestock, the nutritive material is some type of grain product. The majority of the feed composition can be nutritive material with the effective composition present in an amount sufficient to obtain the desired result. Typically, the effective composition is present in an amount between about 0.05% by weight and about 5% by weight and more preferably between about 0.25% by weight and about 3% by weight and most preferably between about 0.30% by weight and about 1% by weight.

The methods and compositions of the present invention can be used in a wide variety of animals from which humans obtain food. Accordingly, the present method and composition for increasing the breast weight as a percentage of body weight are contemplated for use with any type poultry, including, but not limited to, chickens, ducks, turkeys, geese, quail, and cornish game hens. The present methods and compositions for decreasing mortality and for decreasing occurrence of air sac lesions are contemplated for use with any type of livestock including, but not limited to, beef, pork, and lamb. As used herein, the term "food animal" refers to any animal eaten by humans, including, without limitation, poultry and livestock.

EXPERIMENTAL

EXAMPLE 1

A study was conducted on chickens (*Gallus domesticus*) of the strain Arbor Acres X Arbor Acres. On Day 0 of the study, all chicks were 1 day old. The approximate final weight of each at the end of the study was about 5 pounds. The test birds were given one of four treatments: control, virginiamycin at 10 grams per ton, Neosugar G at 0.375%, and Neosugar G at 0.75%. The virginiamycin used is sold under the trademark "STAFAC" by Smith Kline. The treatments were administered in the feed rations of the chickens.

A 22% starter ration was fed for Days 0–21 and a 20% grower-finisher ration was fed from Day 22 to the end of the study. Starter and grower rations contained coccidiostat-monensin at 100 grams per ton. The monensin used is sold under the trademark "COBAN" by Eli Lilly and Company. Each of the treatments was administered orally in the diet. No contaminants in either the feed or the water were known or identified.

The procedures for the study followed the suggestions for "Controlled Floor-Pen Studies of The FDA". All birds were placed on reused litter. The research facility was cleaned by removing wet litter and top dressing with new wood shavings. The feed was weighed at the time of feeding to avoid any possible weight loss. Sixty male broilers were randomized into each of the forty-eight pens used in the study. All chicks were placed on their respective diets on Day 0 of the study and had ready access to water. Supplemental lighting was provided 24 hours a day. All pens were checked twice daily during the study. Observations included availability of feed and water, heat control for attainment of desired temperature and general observations of birds and litter conditions. Chickens were vaccinated for Newcastle disease via water at Day 5. On Days 18–20, chickens received vaccination for infectious bronchitis to simulate a mild field outbreak. The results of the study at forty-seven days are provided below in Tables 1.1–1.4.

TABLE 1.1

| Treatment | Pen No. | No. Birds Started | Removed | Mortality | Weighed | Avg. Wt. (kg) |
|---|---|---|---|---|---|---|
| Control | 1 | 60 | 1 | 6 | 53 | 2.151 |
|  | 6 | 62 | 2 | 5 | 55 | 2.053 |
|  | 9 | 60 | 1 | 8 | 51 | 2.089 |
|  | 16 | 60 | 1 | 3 | 56 | 2.028 |
|  | 18 | 60 | 0 | 3 | 57 | 2.155 |
|  | 22 | 60 | 1 | 6 | 53 | 2.065 |
|  | 25 | 60 | 1 | 5 | 54 | 2.175 |
|  | 30 | 60 | 1 | 2 | 57 | 1.954 |
|  | 33 | 58 | 1 | 5 | 52 | 2.081 |
|  | 38 | 60 | 0 | 3 | 57 | 2.121 |
| Total and Avg. |  | 600 | 9 | 46 | 545 | 2.087 |

TABLE 1.2

| Virginiamycin | 4 | 60 | 0 | 6 | 54 | 2.084 |
|---|---|---|---|---|---|---|
|  | 5 | 60 | 0 | 4 | 56 | 2.150 |
|  | 11 | 60 | 0 | 8 | 52 | 2.165 |
|  | 15 | 60 | 1 | 4 | 55 | 2.107 |
|  | 19 | 63 | 1 | 12 | 50 | 2.213 |
|  | 23 | 60 | 0 | 3 | 57 | 2.164 |
|  | 28 | 60 | 0 | 7 | 53 | 2.191 |
|  | 31 | 62 | 2 | 5 | 55 | 2.149 |
|  | 34 | 60 | 0 | 3 | 57 | 2.139 |
|  | 37 | 60 | 0 | 7 | 53 | 2.151 |
| Total and Avg. |  | 605 | 4 | 59 | 542 | 2.151 |

TABLE 1.3

| Treatment | Pen No. | No. Birds Started | Removed | Mortality | Weighed | Avg. Wt. (kg) |
|---|---|---|---|---|---|---|
| Neosugar G, (.375%) | 2 | 61 | 1 | 9 | 51 | 2.208 |
|  | 7 | 60 | 0 | 3 | 57 | 2.176 |
|  | 10 | 60 | 0 | 6 | 54 | 2.257 |
|  | 14 | 60 | 0 | 8 | 52 | 2.217 |
|  | 17 | 60 | 0 | 2 | 58 | 2.153 |
|  | 24 | 60 | 0 | 7 | 53 | 2.249 |
|  | 26 | 60 | 1 | 2 | 57 | 2.217 |
|  | 29 | 60 | 0 | 3 | 57 | 2.175 |
|  | 36 | 60 | 0 | 3 | 57 | 2.238 |
|  | 39 | 60 | 0 | 8 | 52 | 2.164 |
| Total and Avg. |  | 601 | 2 | 51 | 548 | 2.205 |

TABLE 1.4

| Neosugar G, (.75%) | 3 | 60 | 2 | 6 | 52 | 2.217 |
|---|---|---|---|---|---|---|
|  | 8 | 60 | 0 | 2 | 58 | 2.134 |
|  | 12 | 60 | 1 | 2 | 57 | 2.154 |
|  | 13 | 62 | 0 | 1 | 61 | 2.079 |
|  | 20 | 58 | 0 | 1 | 57 | 2.111 |
|  | 21 | 60 | 0 | 6 | 54 | 2.154 |
|  | 27 | 60 | 0 | 4 | 56 | 2.155 |
|  | 32 | 60 | 1 | 3 | 56 | 2.179 |
|  | 35 | 60 | 0 | 3 | 57 | 2.184 |

TABLE 1.4-continued

|  | 40 | 62 | 0 | 4 | 58 | 2.088 |
|---|---|---|---|---|---|---|
| Total and Avg. |  | 602 | 4 | 32 | 566 | 2.145 |

A summary of the results of Example 1 are provided below in Table 1.5.

TABLE 1.5

| Treatment | Body Weight (Kg) | Feed Eff. | % Mortality | % Hot Weight | % Chilled Weight | % Breast Weight |
|---|---|---|---|---|---|---|
| Control | 2.087 | 1.92 | 7.67 | 67.28 | 69.19 | 17.49 |
| Virginiamycin | 2.151 | 1.93 | 9.71 | 67.88 | 70.02 | 17.83 |
| Neosugar G (.375%) | 2.205 | 1.93 | 8.48 | 67.91 | 69.90 | 18.72 |
| Neosugar G (.75%) | 2.145 | 1.91 | 5.31 | 67.67 | 69.66 | 17.62 |

From the above Example 1, it can be seen that the Neosugar G treatments were effective in the measurements which were taken. In particular, it should be noted that the 0.375% Neosugar G treatment demonstrated a significant body weight advantage over other treatments, and particularly, produced chickens having the highest breast weight as a percentage of body weight. Also, in particular, the 0.75% Neosugar G treatment produced a significantly lower mortality rate than other treatments.

EXAMPLE 2

A study was conducted using 2,400 male Arbor Acre broiler poults which were divided into five groups of 480 birds per treatment. The test was conducted according to procedures outlined in the "Controlled Floor-Plan Studies of the FDA". All of the birds were vaccinated for Newcastle disease via water at Day 5. On Days 14–18, the birds received vaccination for infectious bronchitis to simulate a mild field outbreak. The birds were also stressed by lowering the house temperature 7–10 days after vaccination.

The rations fed to the birds are shown below in Table 2.1.

TABLE 2.1

| Ingredient | Starter | Grower | Finisher |
|---|---|---|---|
| Corn/Wheat | 59.12% | 64.18% | 69.30% |
| Fat | 4.00 | 4.00 | 4.00 |
| Meat Meal | 5.00 | 5.00 | 5.00 |
| Soybean Meal | 30.00 | 25.00 | 20.00 |
| dl-Methionine | 0.18 | 0.17 | 0.10 |
| Defl. Phos. | 1.25 | 1.20 | 1.15 |
| Salt | 0.25 | 0.25 | 0.25 |
| Trace Minerals | 0.05 | 0.05 | 0.05 |
| Vitamin Premix | 0.15 | 0.15 | 0.15 |
| Protein | 22.00 | 20.00 | 18.00 |
| Fat | 6.50 | 6.70 | 6.85 |
| Fiber | >3.00 | >3.30 | >3.50 |
| Ca | 1.06 | 1.04 | 1.02 |
| Phos. avail. | 0.63 | 0.62 | 0.62 |
| Kcal (M.E.) | 1420.00 | 1450.00 | 1480.00 |

Five different treatments were used in the study. Treatment I was a control group. Treatment 2 consisted of adding a commercial antibiotic (bacitracin MD) at the recommended level to the chicken diet. Treatment 3 consisted of adding 0.25% Neosugar (75% syrup with the following percentage amounts on a solid basis: glucose-35%; sucrose-10%; $GF_2$-25%; $GF_3$-25% and $GF_4$-5%) to the chicken diet. Treatment 4 consisted of 0.25% Neosugar added to the chicken diet from Days 21–46 for the entire test period. Treatment 5 consisted of 0.50% Neosugar added to the chicken diet for the entire test period. All chickens had ready access to water, and supplemental lighting was provided 24 hours per day.

A summary of the average body weight, mortality, and air sac lesion scores at 46 days are provided below in Tables 2.2, 2.3, and 2.4.

TABLE 2.2

| Rank | Treatment | | Body Weight (Kg) |
|---|---|---|---|
| 1 | 5 (0.50% Neo.), | 0–46 days | 1.863 |
| 2 | 4 (0.25% Neo.), | 21–46 days | 1.840 |
| 3 | 3 (0.25% Neo.), | 0–46 days | 1.838 |
| 4 | 1 Control | — | 1.811 |
| 5 | 2 Antibio, | 0–15 days | 1.785 |

TABLE 2.3

| Rank | Treatment | | % Mortality |
|---|---|---|---|
| 1 | 5 (0.50% Neo.), | 0–46 days | 4.18 |
| 2 | 2-Antibio, | 0–15 days | 7.07 |
| 3 | 4 (0.25% Neo.), | 21–46 days | 8.32 |
| 4 | 1 Control | — | 8.96 |
| 5 | 3 (0.25% Neo.), | 0–46 days | 10.03 |

TABLE 2.4

| Rank | Treatment | | Air Sac Lesion Score |
|---|---|---|---|
| 1 | 3 (0.25% Neo.), | 0–46 days | 1.54 |
| 2 | 5 (0.50% Neo.), | 0–46 days | 1.54 |
| 3 | 4 (0.25% Neo.), | 21–46 days | 1.94 |
| 4 | 1 Control | — | 2.29 |
| 5 | 2 Antibio, | 0–15 days | 2.44 |

The Neosugar treatments of Example 2 were effective in the various measurements which were taken. Treatment 5, the highest amount of Neosugar, appears to have significantly reduced the mortality rate for that Treatment group. Treatments 3 and 5, in which Neosugar was fed throughout the entire study, produced a significant reduction in the occurrence of air sac lesions.

While various embodiments of the present invention have been described in detail, it is apparent that modifications and adaptations of these embodiments will occur to those skilled in the art. However, it is to be expressly understood that such modifications and adaptations are within the scope of the present invention, as set forth in the following claims.

What is claimed is:

1. A method for raising poultry, comprising feeding said poultry a composition including an effective amount of fructooligosaccharides to enhance the breast weight to body weight ratio of said poultry.

2. A method as claimed in claim 1, wherein said composition includes compounds selected from the group consisting of 1-kestose, nystose, 1-fructofuranosyl nystose and mixtures thereof.

3. A method as claimed in claim 1, wherein said composition comprises between about 20% by weight and about 40% by weight 1-kestose, between about 20% by weight and about 50% by weight nystose, and between about 5% by weight and about 15% by weight 1-fructofuranosyl nystose.

4. A method as claimed in claim 1, wherein said fructooligosaccharides are sucrose molecules having from 1 to 8 fructose residues attached to the sucrose molecules.

5. A method as claimed in claim 1, wherein said fructooligosaccharides comprise between about 0.05% by weight and about 5.0% by weight of said poultry's food supply.

6. A method, as claimed in claim 1, wherein said composition is fed to said poultry throughout the entire lifetime of said poultry.

7. A method, as claimed in claim 1, wherein said composition is fed to said poultry by mixing said composition with said poultry's food rations.

8. A method for reducing food animal mortality prior to being killed for consumption by humans, comprising feeding to said food animals a composition comprising an effective amount of fructooligosaccharides to reduce food animal mortality prior to being killed for consumption by humans.

9. A method for reducing the incidence of air sac lesions in food animals, comprising feeding to said food animals a composition comprising an effective amount of fructooligosaccharides to reduce the incidence of air sac lesions.

10. A method as claimed in claims 8 or 9, wherein said food animals are chickens.

11. A method as claimed in claims 8 or 9, wherein said composition includes compounds selected from the group consisting of 1-kestose, nystose, 1-fructofuranosyl nystose and mixtures thereof.

12. A method as claimed in claims 8 or 9, wherein said composition comprises between about 20% by weight and about 40% by weight 1-kestose, between about 20% by weight and about 50% by weight nystose, and between about 5% by weight and about 15% by weight 1-fructofuranosyl nystose.

13. A method as claimed in claims 8 or 9, wherein said fructooligosaccharides are sucrose molecules having from 1 to 8 fructose residues attached to the sucrose molecules.

14. A method as claimed in claims 8 or 9, wherein said fructooligosaccharides comprise between about 0.05% by weight and about 5.0% by weight of said food animals' food supply.

15. A method as claimed in claims 8 or 9, wherein said composition is fed to said food animals throughout the entire lifetime of said food animals.

16. A method as claimed in claims 8 or 9, wherein said composition is fed to food animals by mixing said composition with said food animals' food rations.

17. A method for increasing the body weight of poultry and for increasing the breast weight of said poultry as a percentage of body weight, comprising orally administering an effective amount of fructooligosaccharides to said poultry in admixture with said poultry's food supply to increase body weight and to increase breast weight as a percentage of body weight.

18. A method for decreasing the mortality of poultry prior to being killed for consumption by humans, comprising orally administering an effective amount of fructooligosaccharides to said poultry in admixture with said poultry's food supply to decrease mortality prior to being killed for consumption by humans.

* * * * *